United States Patent [19]

Thaisrivongs

[11] Patent Number: 4,882,420
[45] Date of Patent: Nov. 21, 1989

[54] DIHALO-STATINE SUBSTITUTED RENIN INHIBITORS

[75] Inventor: Suvit Thaisrivongs, Kalamazoo, Mich.

[73] Assignee: The Upjohn Company, Kalamazoo, Mich.

[21] Appl. No.: 934,540

[22] PCT Filed: Apr. 7, 1986

[86] PCT No.: PCT/US86/00713

§ 371 Date: Nov. 28, 1986

§ 102(e) Date: Nov. 28, 1986

[87] PCT Pub. No.: WO86/06379

PCT Pub. Date: Nov. 6, 1986

Related U.S. Application Data

[63] Continuation-in-part of Ser. No. 828,407, Feb. 11, 1986, abandoned, which is a continuation-in-part of Ser. No. 725,190, Apr. 19, 1985, abandoned.

[51] Int. Cl.$^4$ .......................... C07K 5/08; C07K 5/10; C07K 7/06
[52] U.S. Cl. ...................................... 530/330; 530/331
[58] Field of Search ................................ 530/330, 331

[56] References Cited

U.S. PATENT DOCUMENTS

| 4,424,207 | 1/1984 | Szelke et al. | 424/177 |
| 4,470,971 | 9/1984 | Boger et al. | 424/177 |
| 4,478,826 | 10/1984 | Verber et al. | 424/177 |

FOREIGN PATENT DOCUMENTS

| 0045161 | 7/1981 | European Pat. Off. | 103/50 |
| 0045665 | 8/1981 | European Pat. Off. | 103/52 |
| 0053017 | 11/1981 | European Pat. Off. | 401/06 |
| 0077028 | 10/1982 | European Pat. Off. | 103/52 |
| 0077029 | 10/1982 | European Pat. Off. | 103/52 |
| 0081783 | 12/1982 | European Pat. Off. | 103/52 |
| 0104041 | 9/1983 | European Pat. Off. | 103/52 |
| 0111266 | 12/1983 | European Pat. Off. | 103/52 |
| 0114993 | 12/1983 | European Pat. Off. | 103/52 |
| 0118223 | 9/1984 | European Pat. Off. | 37/64 |
| 0129189 | 12/1984 | European Pat. Off. | |
| 0156321 | 10/1985 | European Pat. Off. | |
| 0157409 | 10/1985 | European Pat. Off. | |
| 0173481 | 3/1986 | European Pat. Off. | |
| 3604510 | 8/1986 | Fed. Rep. of Germany | |

OTHER PUBLICATIONS

Chem. Abstr., vol. 102, (1985), 181341.
Chem. Abstr., vol. 101, (1984), 210370.
Chem. Abstr., vol. 106, (1987), 85059.
Chem. Abstr., vol. 103, (1985), 160849.
Chem. Abstr., vol. 105, (1986), 153525.
Chem. Abstr., vol. 101, (1984), 7608.
Chem. Abstr., vol. 101, (1984), 23943.
Chem. Abstr., vol. 106 (1987), 214385.
Tetrahedron Letters, vol. 24, No. 41, pp. 4401–4404 (1983).
Tetrahedron Letters, vol. 25, No. 22, pp. 2301–2303 (1984).
Brandange et al., J. Am. Chem. Soc., 103, 4452 (1981).
par Bertrand Castro et al., Bull. Soc. Chim. Fr., 3521 (1969).
S. Thaisrivongs et al., "Difluorostatine–and difluorostatone–containing peptides as potent and specific renin inhibitors", J. Med. Chem., vol. 28, No. 11, Nov. 1985, pp. 1553–1555.

*Primary Examiner*—Delbert R. Phillips
*Attorney, Agent, or Firm*—Lawrence T. Welch

[57] ABSTRACT

The present invention provides novel renin inhibitory peptides of the formula X—A—B—C—D—E—F—G—H—Z wherein E—F is a dihalo-substituted statine group, X and Z are terminal groups, and the remaining variables are absent or amino acid residues. These compounds are useful for administration to humans to treat hypertension.

8 Claims, No Drawings

DIHALO-STATINE SUBSTITUTED RENIN INHIBITORS

CROSS REFERENCE TO RELATED APPLICATIONS

This application is a continuation-in-part of co-pending application Ser. No. 828,407, filed Feb. 11, 1986, now abandoned, which is a continuation-in-part of Ser. No. 725,190, filed Apr. 19, 1985, now abandoned.

BACKGROUND OF THE INVENTION

The present invention provides novel renin-inhibiting peptides and intermediates for their preparation. Such inhibitors are useful for the diagnosis and control of renin-dependent hypertension.

INFORMATION DISCLOSURE

The preparation and use of certain renin-inhibiting peptides is found in U.S. Pat. No. 4,424,207 which is incorporated herein by reference. Further, EP publication No. 0 118 223 filed Feb. 6, 1984 having U.S. priority application Ser. No. 469,540 and Great Britain Application No. 8,322,414 filed Aug. 19, 1983 also disclose renin inhibiting peptide analogs. Additionally, Holladay et al., in "Synthesis of Hydroxyethylene and Ketomethylene Dipeptide Isosteres", *Tetrahedron Letters,* Vol. 24, No. 41, pp. 4401–4404, 1983 disclose various intermediates in a process to prepare stereo-directed "ketomethylene" and "hydroxyethylene" dipeptide isosteric functional groups disclosed in the above noted U.S. Pat. No. 4,424,207. Holladay et al., first synthesized an acid which is then incorporated into peptides as disclosed by the references cited therein including EP application 45665. U.S. Pat. No. 4,424,207 in the U.S. patent corresponding to this EP document. See also EP publication Nos. 77028, 77029, 81783, 104041, 111266 and 114993 and U.S. Pat. Nos. 4,470,971 and 4,478,826.

Additionally, European Applications 0 045 161 and 0 053 017 disclose amide derivatives useful as inhibitors of angiotensin converting enzymes. Hallinan, et al., in Tetrahedron Letters, 25:2301-2302 (1984) discloses the preparation of 2,2-difluoro-3-hydroxy esters by the Reformatskii reaction. Brandange, et al., J. Am. Chem. Soc., 103, 4452 (1981) discloses the preparation of 2-fluoro-3-hydroxy esters. Castro, et al., Bull. Soc. Chim. Fr., 3521 (1969) discloses the preparation of 2,2-dichloro-3-hydroxy esters.

SUMMARY OF THE INVENTION

The present invention provides: a renin inhibitory peptide of the formula II: X—A—B—C—D—E—F—G—H—Z, wherein X is
(a) hydrogen,
(b) $R_{x1}$—,
(c) $R_{x1}$—$V_{x1}$—C($R_{x2}$)($R_{x3}$)CO—,
(d) $R_{x4}$—N($R_{x4}$)(CH$_2$)$_{0-6}$—CO—,
(e) $R_{x5}$—O—CO—(CH$_2$)$_{1-6}$—CO—,
(f) $R_{x5}$—N—($R_{x5}$)—CO—(CH$_2$)$_{1-6}$—CO—,
(g) $R_{x4}$—SO$_2$—N($R_{x5}$)(CH$_2$)$_{1-6}$—CO—,
(h) $R_{x4}$—N($R_{x4}$)(CH$_2$)$_{0-6}$—SO$_2$—(CH$_2$)$_{1-6}$—CO—,
(i) Arg—,
(j) Arg—Arg—,
(k) $R_{x6}$—O—CH$_2$—CO—,
(l) $R_{x6}$—CH$_2$—O—CO—,
(m) $R_{x6}$—O—CO—, or
(n) $R_{x6}$—(CH$_2$)$_{0-6}$—CO—;

wherein —A— is absent or a divalent moiety of the formula IIA;
wherein —B— is absent or a divalent moiety of the formula IIB;
wherein —C— is absent or a divalent moiety of the formula IIC;
wherein —D— is a divalent moiety of the formula IID;
wherein —E—F— is a divalent moiety of the formula IIEF;
wherein —G— is absent or a divalent moiety of the formula IIG;
wherein —H— is absent or a divalent moiety of the formula IIH;
wherein Z is
(a) —$V_{z1}$—(CH$_2$)$_{0-6}$—$R_{z1}$,
(b) —$V_{z1}$—CH$_2$—(C$_1$-C$_5$hydroxyalkyl),
(c) —$V_{z1}$—CH$_2$—(C$_1$-C$_5$aminoalkyl),
(d) —$V_{z1}$—CH$_2$—((C$_1$-C$_5$alkyl)—(mono—, di—, or tri—C$_1$—C$_5$alkyl)amino,
(e) —$V_{z1}$—CH$_2$—((C$_1$-C$_5$alkyl)-guanidyl),
(f) d or l—Lys—OH,
(g) d or l—Lys—NH$_2$,
(h) d or l—Ser—OH, or
(i) d or l—Ser—NH$_2$;

wherein Y is —N($R_{8c}$)— or divalent oxygen (—O—);
with the provisos that
(1) when Y is absent or —N($R_{8c}$)—, X is
(a) hydrogen,
(b) $R_{x1}$—,
(c) $R_{x1}$—$V_{x1}$—C($R_{x2}$)($R_{x3}$)C0—,
(d) $R_{x4}$—N($R_{x4}$)(CH$_2$)$_{0-6}$—CO—,
(e) $R_{x5}$—O—CO—(CH$_2$)$_{1-6}$—CO—,
(f) $R_{x5}$—N—($R_{x5}$)—CO—(CH$_2$)$_{1-6}$—CO—,
(g) $R_{x4}$—SO$_2$—N($R_{x5}$)(CH$_2$)$_{1-6}$—CO—,
(h) $R_{x4}$—N($R_{x4}$)(CH$_2$)$_{0-6}$—SO$_2$—(CH$_2$)$_{1-6}$—CO—,
(i) Arg—, or
(j) Arg—Arg—; and
(2) when Y is —O—, A and B are both absent and X is
(a) hydrogen,
(b) $R_{x6}$—O—CH$_2$—CO—,
(c) $R_{x6}$—CH$_2$—O—CO—,
(d) $R_{x6}$—O—CO—,
(e) $R_{x6}$—(CH$_2$)$_{0-6}$—CO—, or
(f) $R_{x5}$—N($R_{x5}$)—CH$_2$—CO—;

wherein —U— is
(a) —C(O)—,
(b) —CH(OH)—, or
(c) —CH(NH$_2$)—;

wherein W$_1$ and W$_2$ are the same or different and are
(a) fluoro,
(b) chloro,
(c) bromo, or
(d) hydrogen, with the proviso that W$_1$ and W$_2$ are not hydrogen simultaneously;

wherein $R_{x1}$ is
(a) $R_{x4}$—(CH$_2$)$_{0-2}$—,
(b) $R_{x4}$—CO—,
(c) $R_{x4}$—(CH$_2$)$_{0-5}$—O—CO, wherein $R_{x4}$ is not hydrogen,
(d) $R_{x4}$—(CH$_2$)$_{1-5}$—CO—,
(e) $R_{x4}$—(CH$_2$)$_{0-4}$—SO$_2$—,
(f) $R_{x4}$—SO$_2$—(CH$_2$)$_{0-4}$—, with the proviso that $V_{x1}$ is other than oxygen for (CH$_2$)$_0$, or (g) $R_{x4}$—$SO_2$—$(CH_2)_{2-4}$—O—CO—;
wherein $R_{x2}$ is
 (a) hydrogen,
 (b) $C_1$-$C_8$alkyl,
 (c) $C_3$-$C_7$cycloalkyl,
 (d) aryl,
 (e) heterocycle,
 (f) —CH($R_{x3}$)—aryl,
 (g) —CH($R_{x3}$)—heterocycle;
 (h) —$CH_2CH_2$—aryl,
 (i) —$CH_2CH_2$—heterocycle,
 (j) —OH,
 (k) —CH($R_{x3}$)—OH,
 (l) —CH($R_{x3}$)—SH,
 (m) —CH($R_{x3}$)—$OCH_3$, or
 (n) —CH($R_{x3}$)—$SCH_3$;
wherein $R_{x3}$ is
 (a) hydrogen or
 (b) $C_1$-$C_3$alkyl;
wherein $R_{x4}$ is
 (a) hydrogen,
 (b) $C_1$-$C_7$alkyl,
 (c) $C_3$-$C_7$cycloalkyl,
 (d) —$CH_2$—($C_1$-$C_4$hydroxyalkyl),
 (e) —$CH_2$—($C_1$-$C_4$aminoalkyl),
 (f) aryl or
 (g) heterocycle;
wherein $R_{x5}$ is
 (a) hydrogen or
 (b) $C_1$-$C_6$alkyl;
wherein $R_{x6}$ is
 (a) $C_1$-$C_6$alkyl,
 (b) $C_3$-$C_7$alkyl,
 (c) aryl, or
 (d) heterocycle;
wherein $R_{6a}$ is
 (a) hydrogen, or
 (b) $C_1$-$C_3$alkyl;
wherein $R_{6b}$ is —[CH($R_{6e}$)]$_{0-3}$—$R_{6f}$;
wherein $R_{6c}$ is
 (a) hydrogen, or
 (b) $C_1$-$C_3$alkyl;
wherein $R_{6e}$ is
 (a) hydrogen, or
 (b) $C_1$-$C_3$alkyl;
wherein $R_{6f}$ is
 (a) hydroxy,
 (b) $C_1$-$C_6$alkyl,
 (c) $C_3$-$C_{10}$cycloalkyl,
 (d) aryl,
 (e) heterocycle,
 (f) —$(CH_2)_{0-3}$—SH,
 (g) $C_7$-$C_{14}$bi- or tricycloalkyl,
 (h) $C_1$-$C_4$hydroxyalkyl,
 (i) $C_1$-$C_3$alkyloxy,
 (j) $C_1$-$C_3$alkyloxy-($C_1$-$C_4$alkyl)—,
(k) aryl—O—,
 (l) aryl—O—($C_1$-$C_4$alkyl)—,
 (m) aryl—$CH_2$—O—, or
 (n) aryl—$CH_2$—O—($C_1$-$C_4$alkyl)—;
wherein $R_{7a}$ is
 (a) hydrogen, or
 (b) $C_1$-$C_3$alkyl;
wherein $R_{7s}$ is
 (a) —$(CH_2)_3$—, or
 (b) a divalent substituent of the formula 7A, 7B, 7C, 7D, 7E, 7F, or 7G;
wherein $R_{8a}$ is
 (a) hydrogen, or
 (b) $C_1$-$C_3$alkyl;
wherein $R_{8b}$ is —[CH($R_{6e}$)]$_{0-3}$—$R_{6f}$;
wherein $R_{8c}$ is
 (a) hydrogen, or
 (b) $C_1$-$C_3$alkyl;
wherein $R_{9a}$ is
 (a) hydrogen, or
 (b) $C_1$-$C_3$alkyl;
wherein $R_{9b}$ is —[CH($R_{9e}$)]$_{0-3}$—$R_{9f}$;
wherein $R_{9c}$ is
 (a) hydrogen, or
 (b) $C_1$-$C_3$alkyl;
wherein $R_{9e}$ is
 (a) hydrogen, or
 (b) $C_1$-$C_3$alkyl;
wherein $R_{9f}$ is
 (a) hydrogen,
 (b) aryl,
 (c) heterocycle,
 (d) $C_1$-$C_6$alkyl,
 (e) $C_3$-$C_{10}$cycloalkyl,
 (f) $C_7$-$C_{14}$bi- or tricycloalkyl,
 (g) —$NH_2$,
 (h) —OH,
 (i) $C_1$-$C_4$aminoalkyl,
 (j) $C_1$-$C_4$hydroxyalkyl,
 (k) $C_1$-$C_3$alkyloxy-($C_1$-$c_4$alkyl)—
 (l) —$(CH_2)_{1-6}$—NHC(=NH)$NH_2$,
 (m) —$CH_2SCH_3$,
 (n) —$(CH_2)_{0-4}$CO—$R_{9d}$,
 (o) —O-aryl,
 (p) —O—$CH_2$-aryl,
 (q) —($C_1$-$C_4$alkyl)—O—aryl,
 (r) —($C_1$-$C_4$alkyl)—O—$CH_2$—aryl,
 (s) —O—$CH_2$-heterocycle, or
 (t) —($C_1$-$C_4$alkyl)-O—$CH_2$-heterocycle;
wherein $R_{9d}$ is
 (a) hydrogen,
 (b) $NH_2$, or
 (c) $C_1$-$C_3$alkyloxy;
wherein $R_{10a}$ is
 (a) hydrogen, or
 (b) $C_1$-$C_3$alkyl;
wherein $R_{10b}$ is
 (a) $C_1$-$C_7$alkyl,
 (b) $C_3$-$C_7$cycloalkyl,
 (c) —$(CH_2)_{1-4}$—($C_3$-$c_7$cycloalkyl),
 (d) —$(CH_2)_{1-4}$—aryl,
 (e) —$(CH_2)_{1-4}$—heterocycle,
 (f) $C_5$-$C_7$cycloalkenyl, or
 (g) —$(CH_2)_{1-4}$-($C_5$-$C_7$cycloalkenyl);
wherein $R_{10c}$ is
 (a) hydrogen, or
 (b) $C_1$-$C_3$alkyl;
wherein $R_{12a}$ is
 (a) hydrogen, or
 (b) $C_1$-$C_3$alkyl;
wherein $R_{12b}$ is
 (a) hydrogen, or
 (b) —[CH($R_{12e}$)]$_{0-4}$—$R_{12f}$;
wherein $R_{12c}$ is
 (a) hydrogen, or
 (b) $C_1$-$C_3$alkyl;
wherein $R_{12e}$ is
 (a) hydrogen, or
 $C_1$-$C_3$alkyl;
wherein $R_{12f}$ is (a) hydrogen,
(b) aryl,
(c) heterocycle,
(d) $C_1$-$C_6$alkyl,
(e) $C_3$-$C_{10}$cycloalkyl, or
(f) $C_7$-$C_{14}$bi- or tricycloalkyl;
(g) hydroxy,
(h) $C_1$-$C_4$hydroxyalkyl,
(i) $C_1$-$C_3$alkyloxy,
(j) $C_1$-$C_3$alkyloxy-($C_1$-$C_4$alkyl)—,
(k) aryl—O—,
(l) aryl—O—($C_1$-$C_4$alkyl)—,
(m) aryl—$CH_2$—O—, or
(n) aryl—$CH_2$—O—($C_1$-$C_4$alkyl)—;
wherein $R_{13a}$ is
(a) hydrogen, or
(b) $C_1$-$C_3$alkyl;
wherein $R_{13b}$ is —[$CH(R_{13e})$]$_{0-4}$—$R_{13f}$;
wherein $R_{13c}$ is
(a) hydrogen, or
(b) $C_1$-$C_3$alkyl;
wherein $R_{13e}$ is
(a) hydrogen, or
(b) $C_1$-$C_3$alkyl;
wherein $R_{13f}$ is
(a) hydrogen,
(b) aryl,
(c) heterocycle,
(d) $C_1$-$C_6$alkyl
(e) $C_3$-$C_{10}$cycloalkyl,
(f) $C_7$-$C_{14}$bi- or tricycloalkyl,
(g) hydroxy,
(h) amino,
(i) $C_1$-$C_4$aminoalkyl,
(j) $C_1$-$C_4$hydroxyalkyl,
(k) $C_1$-$C_3$alkyloxy,
(l) $C_1$-$C_3$alkyloxy—($C_1$-$C_4$alkyl)—,
(m) —($CH_2$)$_{1-6}$—NHC(=NH)$NH_2$,
(n) —$CH_2SCH_3$,
(o) —($CH_{12}$)$_{0-4}$—CO—$R_{13g}$,
(p) aryl—O—,
(q) aryl—O—($C_1$-$C_4$alkyl)—
(r) aryl—$CH_2$—O—,
(s) aryl—$CH_2$—O—($C_1$-$C_4$alkyl)—
(t) heterocycle—$CH_2$—O—, or
(u) heterocycle—$CH_2$—O—($C_1$-$C_4$alkyl)—;
wherein $R_{13g}$ is
(a) OH,
(b) $NH_2$, or
(c) $C_1$-$C_3$alkyloxy;
wherein $R_{z1}$ is
(a) hydrogen,
(b) $C_1$-$C_7$alkyl,
(c) $C_3$-$C_7$cycloalkyl,
(d) aryl, or
(e) heterocycle; and
wherein $R_{z2}$ is
(a) hydrogen, or
(b) $C_1$-$C_3$alkyl;
wherein $V_{x1}$ is
(a) —$CH_2$—,
(b) —CH($R_{x1}$),
(c) —N($R_{x5}$)—,
(d) —O—;
(e) —S—,
(f) —SO—, or
(g) —$SO_2$—;
wherein $V_{z1}$ is (a) —O—,
(b) —S—, or
(c) —N($R_{z2}$)—;
wherein $V_{7a}$ is
(a) —O—,
(b) —S—, or
(c) —CH(OH)—.

Formula III depicts the moieties A—H when present.
The present invention further relates to a novel intermediate of formula XXX
wherein $W_1$ and $W_2$ are the same or different and are
(a) fluoro,
(b) chloro,
(c) bromo, or
(d) hydrogen, with the proviso that $W_1$ and $W_2$ are not hydrogen simultaneously;
wherein $R_{10a}$ is
(a) hydrogen, or
(b) $C_1$-$C_3$alkyl;
wherein $R_{10b}$ is
(a) $C_1$-$C_7$alkyl,
(b) $C_3$-$C_7$cycloalkyl,
(c) —($CH_2$)$_{1-4}$—($C_3$-$C_7$cycloalkyl),
(d) —($CH_2$)$_{1-4}$—aryl,
(e) —($CH_2$)$_{1-4}$—heterocycle,
(f) $C_5$-$C_7$cycloalkenyl, or
(g) —($CH_2$)$_{1-4}$—($C_5$-$C_7$cycloalkenyl);
wherein $R_{10c}$ is
(a) hydrogen, or
(b) $C_1$-$C_3$alkyl;
wherein $R_{14}$ is
(a) hydrogen,
(b) $C_1$-$C_5$alkyl, or
(c) a pharmacologically acceptable cation; and
wherein $R_{15}$ is
(a) hydrogen, or
(b) an amino protecting group.

When a variable occurs two or more times in a molecule, each occurrence is independently selected from the set of definitions for that variable. The term alkyl means alkyl of the indicated number of carbon atoms, inclusive, and includes straight-chain and branched chain forms thereof. The number of carbon atoms is indicated by the prefix to each carbon containing substituent. Thus, for example, $C_1$-$C_3$ indicates a carbon containing moiety of from 1 to 3 carbon atoms. The term cycloalkyl means cycloalkyl of the indicated number of carbon atoms, inclusive, and additionally includes (1) cycloalkyl substituted by alkyl and (2) alkyl substituted by cycloalkyl such that the total number of carbon atoms is in the indicated range. The term aryl means phenyl or naphthyl optionally substituted by one or more —halogen (F, Cl, Br, I), —$CF_3$, $C_1$-$C_6$alkyl, —$OR^{x5}$, —aryl$_1$, —heterocycle, —$SOCH_3$, —$SO_2CH_3$, —$NHSO_2CH_3$, —$NHSO_3Na$, —$NHSO_3K$, —$CO_2R_{x5}$, —$CON(R_{x5})R_{x5}$, —CHO, —$NHSO_2N(R_{x5})R_{x5}$, —S—($C_1$-$C_3$alkyl). The term aryl$_1$ is defined as for aryl except that it cannot contain aryl$_1$ as a substituent. The term heterocycle is defined as a substituent which is any 5- or 6-membered aromatic ring containing from one to three heteroatoms selected from the group consisting of nitrogen, oxygen, and sulfur; being fully unsaturated, partially saturated, or fully saturated; and including any bicyclic group in which any of the above heterocyclic rings is fused to a benzene ring, including (*indicates a preferred group) 2-, 3-, or 4-pyridinyl*, N-formylindolyl*, imidazolyl*, 1,2,4-triazolyl*, thienyl, pyrimidinyl*, furanyl, benzo[b]-thienyl-including oxidized forms of sulfur*, pyrrolyl*, benzthiazolyl, benzoxazolyl, benzimidazolyl*, quinolinyl*, pyrazolyl, pyrazinyl, piperidinyl, pyrrolinyl, pyrrolidinyl, pyrazolinyl, pyrazolidinyl, imidazolinyl, imidazolidinyl, piperazinyl, pyridazinyl, oxazolyl, oxazolidinyl, isoxazolyl, isoxazolidinyl, morpholinyl, thiazolyl, thiazolidinyl, isothazolidinyl, isothazolyl, indolyl, isoquinolinyl; each such heterocycle being optionally substituted by one or more —halogen (F, Cl, Br, I), —$CF_3$, $C_1$–$C_6$alkyl, —$OR_{x5}$, aryl, heterocycle$_1$, —$SOCH_3$, —$SO_2CH_3$, —$NHSO_2CH_3$, —$NHSO_3Na$, —$NHSO_3K$, —$CO_2R^x{}_5$, —CO—$N(R_{x5})R_{x5}$, —CHO, —$NHSO_2N(R_{x5})R_{x5}$, —S—($C_1$–$C_3$alkyl). The term heterocyclic$_1$ is defined as for heterocycle except that it cannot contain heterocycle$_1$ as a substituent. The numbered subscripts for each bracketed moiety indicate the number of times that moiety could occur. For example, —$(CH_2)_{0-4}$ indicates that the moiety may be absent, or be present from 1 to 4 times. Pharmacologically acceptable cations within the scope of this invention include pharmacologically acceptable metal cations, ammonium, amine cations, or quarternary ammonium cations. Especially preferred metal cations are those derived from the alkali metals, e.g., lithium, sodium, and potassium, and from the alkaline earth metals, e.g., aluminum, zinc, and iron are within the scope of this invention.

The compound of formula XXX is used to prepare the novel renin-inhibitory compounds of this invention which are prepared by incorporating appropriate amino acids into the C-terminal or N-terminal portion of the formula XXX. These amino acids can have either the D- or L-configuration, the chain length can vary depending on the number of amino acids added to the N or C terminal ends of formula XXX and any multiple of the contiguous amino acids may be included in this invention. By this means are provided novel isosteric polypeptides which have renin-inhibiting properties without the nautral peptide sequence, i.e., ProPheHis left of the isosteric moiety as provided in U.S. Pat. No. 4,424,207. In other words, each of the amino acids Pro, Phe, His can be replaced by another appropriate amino acid to provide a novel isosteric polypeptide. For example, Phe can be replaced by dehydro Phe, Tyr, Trp, or 4-ClPhe, and Pro can be replaced by Δ3,4-Pro, 4-hydroxy Pro and thiazolidine-4-carboxacyl. Further, it may be advantageous to alkylate the amide nitrogen with either methyl or ethyl to provide stability to the desired peptide. The N-terminal amino acid can be acylated by carboxylic acids such as acetic, isobutyric, isovaleric, hydrocinnamic, propionic, benzoic, α-phenyl acetic acids. The C terminal amino acid can be derivatized to give esters of lower alkanols and amides of amines such as $NH_3$, $NH_2$—$CH_3$, $NH_2$—Et, $NH_2$—$CH_2CH_2N(CH_3)CH_3$, $NH_2(CH_2)_n$—$NH_2$, $NH(CH_2)_n$—NH—C(=NH)—$NH_2$ wherein n is limited to two to five carbons, inclusive.

N-alkyl His, where appropriate as a starting material in the present invention, is prepared as described in published European Patent Application 173,481 (5 March 1986).

In all of the processes of the present invention, the starting materials are either known or can be prepared by known methods.

Certain compounds of this invention are preferred. Thus, preferred are compounds of the formula II:
 wherein X is
  (a) hydrogen,
  (b) $CH_3CO$—,
  (c) $(CH_3)_3C$—O—CO—, or
  (d) $(CH_3)_3C$—$CH_2$—CO—;
wherein $R_{6a}$ and $R_{6c}$ are hydrogen;
wherein $R_{6b}$ is
  (a) benzyl,
  (b) (2-naphthyl)methyl,
  (c) $N^{in}$-formylindole-3-methyl-,
  (d) 1H-imidazole-4-methyl-, or
  (e) (1-naphthyl-)methyl-
wherein $R_{7s}$ is —$(CH_2)_3$—;
wherein $R_{7a}$ is
  (a) hydrogen, or
  (b) $CH_3$;
wherein $R_{8a}$ and $R_{8c}$ are hydrogen;
where $R_{8b}$ is
  (a) benzyl,
  (b) (2-naphthyl)methyl,
  (c) $N^{in}$-formylindole-3-methyl, or
  (d) (1-naphthyl-)methyl);
wherein $R_{9c}$ is hydrogen, or $CH_3$;
wherein $R_{9a}$ is hydrogen;
wherein $R_{9b}$ is
  (a) benzyl,
  (b) p-chloro-benzyl,
  (c) 1H-imidazole-4-methyl-,
  (d) (2-, 3-, or 4-pyridinyl)-methyl-, or
  (e) $C_1$–$C_3$alkyl;
wherein $R_{10a}$ and $R_{10c}$ are hydrogen;
wherein $R_{10b}$ is
  (a) 2-methylpropyl,
  (b) benzyl, or
  (c) cyclohexylmethyl;
wherein $W_1$ and $W_2$ are fluorine;
wherein —G— is a divalent moiety of the formula IIG;
wherein $R_{12a}$ and $R_{12c}$ are hydrogen;
wherein $R_{12b}$ is
  (a) hydrogen,
  (b) —$CH_3$,
  (c) —$CH_2CH_3$,
  (d) —$CH(CH_3)_2$,
  (e) —$CH_2CH(CH_3)_2$ or
  (f) —$CH(CH_3)CH_2CH_3$;
wherein —H— is absent;
wherein —Z— is
  (a) OH,
  (b) $NH_2$,
  (c) phenyl-($C_1$–$C_3$alkyl)amino-,
  (d) (2-, 3-, or 4-pyridinyl)-($C_1$–$C_3$-alkyl)-amino-, or
  (e) $C_1$–$C_6$alkyl-amino-;
and all other variables are as defined above.

Chiral centers may be of the R or S configuration, however, S is preferred, e.g., in the case of naturally occurring amino acid moieties. For other chiral centers, the analogous configuration is preferred, although the assignment of R and S configuration may change, depending on the substituents of the compound. For example the hydroxy-bearing carbon atom of statine has the S configuration, but the same carbon of 2,2-difluorostatine (same absolute configuration) has the R configuration. This is indicated by the phrase "S or analogous configuration."

Preferred compounds are N-tert-butyloxycarbonyl-L-phenylalanyl-L-histidyl-4S-amino-2,2-difluoro-3R-hydroxy-4-(2-methylpropyl)-1-oxobutyl-L-isoleucyl-2-pyridylmethylamide; N-tert-butyloxycarbonyl-L-phenylalanyl-L-histidyl-4-amino-2,2-difluoro-4-(2-methylpropyl)-1,3-dioxobutyl-L-isoleucyl-2-pyridylmethylamide; N-tert-butyloxycarbonyl-L-phenylalanyl-L-histidyl-4S-amino-2,2-difluoro-3R-hydroxy-4-phenylmethyl-1-oxobutyl-L-isoleucyl-2-pyridylmethylamide; N-tert-butyloxycarbonyl-L-phenylalanyl-L-histidyl-4-amino-2,2-difluoro-4-phenylmethyl-1,3-dioxobutyl-L-isoleucyl-2-pyridylmethylamide; N-tert-butyloxycarbonyl-L-phenylalanyl-L-histidyl-4S-amino-4-cyclohexylmethyl-2,2-difluoro-3R-hydroxy-1-oxobutyl-L-isoleucyl-2-pyridylmethylamide; and N-tert-butyloxycarbonyl-L-phenyalanyl-L-histidyl-4-amino-4-cyclohexylmethyl-2,2-difluoro-1,3-dioxobutyl-L-isoleucyl-2-pyridylmethylamide.

A method of using the renin-inhibiting peptide analogs of the present invention is described in U.S. Pat. No. 4,424,207 which is expressly incorporated by reference herein.

All the renin-inhibitory compounds of the present invention may be administered in the conventional forms, such as those disclosed in the U.S. Pat. No. 4,424,207. Likewise, the dosage amounts disclosed in the U.S. Pat. No. 4,424,207 are examples applicable to the compounds of the present invention.

The renin inhibitors of this invention are useful for treating any medical condition for which it is beneficial to reduce the levels of active circulating renin. Examples of such conditions include renin-dependent hypertension, hypertension, hypertension under treatment with another antihypertensive and/or a diuretic agent, congestive heart failure, angina, and post-myocardial infarction.

Further, the renin inhibitors of this invention may be useful in the treatment of cerebrovascular disorders and disorders of intracellular homeostasis. The possible role of the renin-angiotension system in the maintenance of intracellular homeostasis is disclosed in Clinical and Experimental Hypertension, 86, 1739–1742 (1984).

Additionally the renin inhibitors of this invention potentiate the antithrombotic activity of a thromboxane antagonist (U.S. Pat. No. 4,558,037). Also, the antihypertensive effect of the renin inhibitors of this invention is potentiated by combination with a thromboxane synthetase inhibitor.

Preferably, compositions containing compounds of the present invention are used for oral administration for treatment of humans for the purpose of reducing blood pressure.

The compounds of this invention may be administered from 0.1 mg to 100 mg per kg per dose, administered from 1 to 4 times daily.

The exact dose depends on the age, weight, and condition of the patient and on the frequency and route of administration. Such variations are within the skill of the practitioner or can readily be determined.

Although dosages herein and in the claims are related to the free base content where compounds are in salt form, the compounds of the present invention may be in the form of pharmaceutically acceptable salts both those which can be produced from the free bases by methods well known in the art and those with which acids have pharmacologically acceptable conjugate bases.

Activity for the novel renin-inhibiting peptides of the present invention of formula II may also be determined in the following manner.

Lyophilized human plasma with 0.1% EDTA is obtained from New England Nuclear, North Billerica, Mass. 01862 as "Plasma Renin Activity Control". This lyophilized plasma is reconstituted, on the day of the assay, with cold sterile distilled water according to directions on the vial. The plasma renin activity (PRA) of the reconstituted plasma is assayed with "GAMMACOAT [$^{125}$I] Plasma Renin Activity Radioimmunoassay Kit" supplied by Clinical Assays, a Division of Travenol Laboratories, Inc., Cambridge, Mass. 02139. The procedure used with these kits is carried out essentially as described in the literature which accompanies them. The initial (enzymatic generation of Angiotensin 1) step is modified slightly to accommodate the testing of renin inhibitors and to minimize the amount of plasma required to perform the assay. Thus, for every milliliter of reconstituted plasma used in the assay, there is added and vortexed 10 $\mu$l of PMSF (0.3M phenylmethylsulfonyl fluoride in ethanol) and 100 $\mu$l of maleate generation buffer, both provided in the kit. 250 $\mu$l of this mixture is then transferred to each tube used in the generation step along with 10 $\mu$l of the potential renin inhibitor suspended or dissolved in 1% Tween 80 in water. This mixture is incubated for 90 minutes at 37° C. in a shaking water bath. Also, in addition to the tubes that incubate at 37° C., 4° C. blanks are run on all compounds assayed as a check for compound-antibody cross reactivity. These 4° C. blanks are identical in volume and composition to those that incubate at 37° C. At the end of the 90 minute incubation, the tubes are placed immediately in an ice water bath to terminate the reaction.

In the case of renin inhibitory peptide (RIP), 100 $\mu$l of the 4° C. blank is added to a GAMMACOAT tube. In these GAMMACOAT tubes, the antibody is immobilized onto the lower inner wall thereby eliminating the need to pipette antibody. Finally, 1 ml of tracer buffer reagent is added to each tube and vortexed. All tubes are allowed to equilibrate for three hours at room temperature. At the end of the equilibration period, the contents of the tubes are decanted. The tubes are then counted in a gamma counter. The results of the RIP are evaluated with the Rodbard Radioimmunoassay Program and the plasma renin activity (PRA) is expressed as mg/ml/hr. Plasma renin activity values obtained for 4° C. blanks are subtracted from the appropriate 37° C. tubes. PRA values from the plasma tubes incubated with compound are compared to the 1% Tween 80 control tubes to yield a percent inhibition. The inhibition results are expressed as $I_{50}$ values which are obtained by plotting two inhibitor concentrations and estimating the concentration producing 50% inhibition. In addition to $I_{50}$ values, relative potencies are also calculated. A relative potency is determined by comparing the $I_{50}$ of RIP to the $I_{50}$ of the compound. However, it must be emphasized that relative potencies are calculated from the $I_{50}$ obtained for RIP on the day the compound is assayed and not from the average $I_{50}$ for RIP.

Using this test system, N-tert-butyloxycarbonyl-L-phenylalanyl-L-histidyl-4S-amino-2,2-difluoro-3R-hydroxy-4-(2-methylpropyl)-1-oxobutyl-L-isoleucyl-2-pyridylmethylamide had an $IC_{50}$ of $1.2 \times 10^{-8}$ and a relative potency of 1,000 and N-tert-butyloxycarbonyl-L-phenylalanyl-L-histidyl-4-amino-2,2-difluoro-4-(2-methylpropyl)-1,3-dioxobutyl-L-isoleucyl-2-pyridylmethylamide had an $IC_{50}$ of $1.4 \times 10^{-9}$ and a relative potency of 6100.

It has been determined that the GAMMACOAT-PRA assay is a suitable replacement for the RENAK assay (supplied by Hoffman-LaRoche and previously known as a diagnostic test for high renin states) to determine the activity of potential renin inhibitors.

The compounds of the present invention may be in either free form or in protected form at one or more of the remaining (not previously protected) peptide, carboxyl, amino, hydroxy, or other reactive groups. The protecting groups may be any of those known in the polypeptide art, amply disclosed in the literature. Compounds of formula XXX are amenable to advantageous synthetic strategies for both polymer supported (U.S. Pat. No. 4,424,207—columns 11 through 17, under EXAMPLES) and solution peptide synthesis. They can be transformed into renin inhibitors of the present invention by standard methods known in the art. For example, the carboxylic acid moiety can be condensed with the amino terminus of suitably protected amino acids or peptides using standard coupling conditions such as dicyclohexylcarbodiimide (DCC)/1-hydroxybenzotriazole (HOBT). The BOC protecting group of the resulting peptides can be selectively removed with 50% trifluoroacetic acid (TFA) $CH_2Cl_2$, and the resulting amino terminus condensed with the free carboxyl group of suitably protected amino acids or peptides again using standard coupling conditions. The resulting protected peptides are then deprotected using standard conditions for the protecting groups employed. The choice of amino acids or peptides used for these condensations is based on the structure of the ultimate renin inhibitor desired. These may be as described in U.S. Pat. No. 4,424,207.

For convenience in naming compounds of this invention made from a compound of the formula XXX, the moiety derived from XXX may be named as a 4-amino-1-oxo-butyl group wherein the amino group forms an amide with the carboxyl group of the fragment of the formula IID and the 1-oxo group is bonded to the fragment IIG or IIH or to Z.

The compounds of the present invention are made as depicted in Chart A. In Chart A, Step 1, the intermediate of formula A-1 is prepared by the reaction of zinc and ethyl bromodifluoroacetate with t-butyloxycarbonyl-L-leucinal to yield the formula A-1 compound and its diastereomer. Corresponding dihalo or monohalo compounds may be prepared by known means, e.g., see Brandänge or Castro, supra or by analogous methods. The corresponding salt is prepared by treating the ester with an appropriate base, e.g., sodium hydroxide. The further incorporation of this moiety into peptidic molecules is accomplished by means well known in the art, e.g., as depicted in Chart A and described in the Examples below. The other peptidic moieties of the present invention are prepared in similar fashion.

Alternatively, in Chart B, L-phenylalaninol is treated with d-tert-butyldicarbonate. The formula B-2 compound thus formed is reacted with oxalyl chloride and dimethyl sulfoxide to yield the formula B-3 compound. This compound is then treated with ethyl dibromodifluoroacetate in the presence of zinc to yield the formula B-4 compound which is incorporated into peptides by the means described herein.

A further description of the means for incorporating the novel intermediate herein into peptidic molecules is described in published European Patent Application No. 173,481 (5 Mar. 1986).

The following definitions and terms in this disclosure are as follows.
Phe is L-phenylalanyl-.
His is L-histidyl-.
Ile is L-isoleucyl-.
$Sta^{2f}$ is 2,2-difluorostatyl which is 4S-amino-2,2-difluoro-3S-hydroxy-4-(2-methylpropyl)-1-oxobutyl- $Sto^{2f}$ is 2,2-difluorostatonyl- which is 4-amino-2,2-difluoro-4-(2-methylpropyl)-1,3-dioxobutyl-.
Pla is phenyl lactoyl (-O-CH($CH_2$-phenyl)-CO-).
Nla is [α-naphthyl]-lactoyl(-O-CH($CH_2$-(α-naphthyl))-CO-).
NOA is [α-naphthoxy]acetyl.
Ac is acetyl.
Trp(CHO) is $N^{in}$-formyl-Trp.
Trp is L-tryptophanyl.
Pro is L-prolyl.
N-Me-His is Nα-methyl-His.
BOC is t-butyloxycarbonyl.
mol is mole.
ml is milliliter.
μl is microliter.
MS (FAB) is mass spectroscopy (fast atom bombardment).
$^1$H-NMR is proton nuclear magnetic resonance.
HPLC is high performance liquid chromatography.
mg is milligrams.
min. is minute.
AMP is pyridine-2-methylamino-.
DCC is dicyclohexylcarbodiimide.
HOBT is 1-hydroxy-benzotriazole.
TFA is trifluoroacetic acid.
DEPC is diethylphosphoryl cyanide.
TEA is triethylamine
Ts is p-toluenesulfonyl.
AHPPA2f is the peptide combining form derived from 4S-amino-2,2-difluoro-3R-hydroxy-5-phenylpentanoic acid.
AHPPA2f3 is as for AHPPA2f except that the stereochemistry is other than 3R,4S (i.e., a mixture of the other three isomers).
ACHPA2f3 is as for ACHPA2f except that the stereochemistry is other than 3R,4S (i.e., a mixture of the other three isomers).
AOPPA2f is the peptide combining form derived from 4-amino-2,2-difluoro-3-oxo-5-phenylpentanoic acid.
ACOPA2f is the peptide combining form derived from 4-amino-5-cyclohexyl-2,2-difluoro-3-oxopentanoic acid which is racemic at C4.
ACHPA2f is the peptide combining form derived from 4S-amino-5-cyclohexyl-2,2-difluoro-3R-hydroxypentanoic acid.
FTrp is $N^{in}$-formyltryptophanyl (i.e., $N^{in}$-formylTrp).
MBA2S is 2S-methylbutylamino.
MBA3 is 3-methylbutylamino.
NLA1S is the peptide combining form derived from 3-(1-naphthyl)-2S-hydroxypropanoic acid where the "N-terminus" is the oxygen of the hydroxy group rather than a nitrogen atom.
NMHis is N(alpha)-methyl-His.
NOA1-naphthyloxyacetyl.

The "peptide combining form derived from an amino acid" is the amino acid with one hydrogen removed from the nitrogen atom which becomes the N-terminus and with the OH removed from the carboxylic carbonyl group which becomes the C-terminus.

The wedge-shaped line indicates a bond which extends above the plane of the paper relative to the plane of the compound depicted thereon.

The dotted line indicates a bond which extends below the plane of the paper relative to the plane of the compound depicted thereon.

RIP means a compound having the formula H-Pro-His-Pro-Phe-His-Phe-Phe-Val-Tyr-Lys-OH.2(CH$_3$C(O)OH).XH$_2$O which is a known renin-inhibiting peptide.

DESCRIPTION OF THE PREFERRED EMBODIMENTS

The present invention is seen more fully by the Examples given below.

PREPARATION 1

Nα-tert-Butyloxycarbonyl-L-phenylalaninol

Chart (B-1 to B-2)

To a stirred solution of 3.024 g (20 mmol) of L-phenylalaninol in 50 ml of dry tetrahydrofuran at 0° C. under argon is added 4.8 g 922 mmol of di-tert-butyl dicarbonate. After stirring at room temperature for 3 hrs, the reaction mixture is then concentrated to give 4.82 g (19.2 mmol, 96%) of the titled alcohol. $^1$H-NMR (CDCl$_3$): δ 1.48, 2.74, 7.25, C#1#4H$_{21}$NO$_3$: Calcd.: C, 66.91; H, 8.42; N, 5.57. Found: C, 66.62; H, 8.35; N, 5.47. IR (mull): 3360, 2925, 1685, 1530, and 1005. [α]$_D$(CHCl$_3$; C=8.795 mg/ml)-24°.

PREPARATION 2

Nα-tert-Butyloxycarbonyl-L-phenylalaninal

Chart B (B-2 to B-3)

To a stirred solution of 0.76 ml (8.7 mmol) of oxalyl chloride in 20 ml of dichloromethane at −78° C. under argon is added 1.36 ml (19.2 mmol) of dimethylsulfoxide in 5 ml of dichloromethane. After 10 min, a solution of 2.0 g (7.96 mmol) of the alcohol of Preparation 1 in 10 ml of dichloromethane is added. After 15 min, 4.4 ml (32 mmol) of triethylamine is added. After warming to room temperature, ice water is added and the resulting mixture is separated. The aqueous layer is extracted with three portions of cold dichloromethane. The combined organic phase is then washed with cold aqueous NaHSO$_4$, cold aqueous NaHCO$_3$, saturated aqueous NaCl, successively. It is then dried (MGSO$_4$), and concentrated.

PREPARATION 3

Ethyl-4-tert-butyloxycarbonylamino-2,2-difluoro-3-hydroxy-5-phenyl-pentanoate

Chart B (B-3 to B-4)

A. Sonicating condition

To a mixture of 118 mg (1.8 mmol) of activated zinc dust and one drop of ethyl bromodifluoroacetate in 0.5 ml of tetrahydrofuran in a sonicating bath is added a solution of 180 mg (0.72 mmol) of the aldehyde of Preparation 3 and 0.23 ml (1.8 mmol) of ethyl bromodifluoroacetate in 1.5 ml of tetrahydrofuran. After a few min, the reaction mixture is filtered and 5 ml of 1M aqueous KHSO$_4$ is added to the filtrate. Tetrahydrofuran is removed under reduced pressure and the reamining aqueous phase is extracted with three 10 ml portions of dichloromethane. The combined organic phase is dried (MgSO$_4$) and then concentrated. The resulting residue is chromatographed on silica gel with 40% ethyl acetate in hexane to give 234 mg (0.63 mmol, 87%) of the titled esters, HPLC indicating a 4:1 mixture of diastereomers.

b. Refluxing conditon

To a stirred mixture of 118 mg (1.8 mmol) of activated zinc dust and one drop of ethyl bromodifluoroacetate in 0.5 ml of tetrahydrofuran in an oil bath at 75° C. is added a solution of 180 mg (0.72 mmol) of the aldehyde of Preparation 3 and 0.23 ml (1.8 mmol) of ethyl bromodifluoroacetate in 1.5 ml of tetrahydrofuran. After a few min, the reaction mixture is allowed to cool and then filtered. The filtrate is diluted with 5 ml of 1M aqueous KHSO$_4$ and then tetrahydrofuran is removed under reduced pressure. The aqueous phase is extracted with three 10 ml portions of dichloromethane. The combined organic phase is dried (MGSO$_4$) and then concentrated. The resulting residue is chromatographed on silica gel with 30% ethyl acetate in hexane to give 216.5 mg (0.58 mmol, 80%) of the esters, HPLC indicating at 10:1 mixture of diasteromers.

Major isomer $^1$H-NMR (CDCl$_3$): δ 1.34, 1.41, 4.31 and 7.28.

M.S. m/z @ 373.1713 (Calc. 373.1701). Recrystallized from EtOAc-hexane: m.p. 137.0=138.6°. Anal. Calcd. for C$_{18}$H$_{25}$NO$_5$F$_2$: C, 57.90; H, 6.75; N, 3.75. Found: C, 57.96; H, 6.52; N, 3.82. IR (mull) 3445, 3230, 2920, 1760, 1680, 1510, and 1105. [α]$_D$ (CHCl$_3$, C=9.835 mg/ml)-30°.

Minor isomer: $^1$H-NMR (CDCl$_3$): δ 1.34, 1.37, 4.38, and 7.28.

M.S. m/z @ 373.1721 (Calc. 373.1701). Recrystallized from EtOAc-hexane: m.p. 117.2°–119.0° Anal. Calcd. for C$_{18}$H$_{25}$NO$_5$F$_2$: C, 57.90; H, 6.75; N, 3.75. Found: C, 57.86; H, 6.74; N, 3.90. IR (mull) 3425, 3360, 2925, 1755, 1700 and 1520. [α]$_D$ (CHCl$_3$, C=8.400 mg/ml)-43°.

PREPARATION 4

2S-tert-Butyloxycarbonylamino-3-cyclohexyl-1-propanol

Chart B (B-3 to B-4)

A mixture of 2.0 g (7.95 mmol) of the alcohol of Preparation 1 and 200 mg of rhodium on alumina in 32 ml of ethanol is shaken at 50 psi of hydrogen for two days. The mixture is filtered and the filtrate concentrated to an oil. It is chromatographed on silica gel with 25% ethyl acetate in hexane to give 1.95 g (7.58 mmol, 95%) of the titled alcohol. $^1$H-NMR (CDCl$_3$): δ 1.44. IR (neat) 3345, 2925, 1690, and 1170. [α]$_D$(CHCl$_3$, C=6.370 mg/ml)-25°. A sample is purified by evaporative distillation: b.p. approximately 160°0.1 1 mmHg. Anal. Calcd. for C$_{14}$H$_{27}$NO$_3$: C, 65.33; H, 10.57; N, 5.44. Found: C, 64.99; H, 10.73; N, 5.41.

PREPARATION 5

2S-tert-Butyloxycarbonylamino-3-cyclohexyl-1-propanal

Chart B (B-2 to B-3)

By the same procedures as in the Preparation of the aldehyde of Preparation 3, 359 mg (1.39 mmol) of the alcohol of Preparation 4, 130 μl (1.49 mmol) of oxalyl chloride, 210 μl (2.96 mmol) of dimethylsulfoxide and 410 μl (2.94 mmol) of triethylamine gave 292 mg (1.14 mmol, 82%) of the titled aldehyde.

PREPARATION 6

Ethyl-4-tert-butyloxycarbonylamino-5-cyclohexyl-2,2-difluoro-3-hydroxy-pentanoate Chart B (B-3 to B-4)

By the same procedure as in the preparation of esters of Preparation 4 by the sonicating condition, 292 mg (1.14 mmol) of the aldehyde of Preparation 5, 200 mg (3.06 mmol) of activated zinc dust, and 390 μl (3.07 mmol) of ethyl bromodifluoroacetate gave 423 mg (1.11 mmol, 97%) of the titled esters as mixture of diastereomers after chromatography on silica gel with 20% ethyl acetate in hexane.

Major isomer: $^1$H-NMR (CDCl$_3$): δ 1.37, 1.45, and 4.32. IR (neat 3400, 2925, 1770, 1690, 1510, and 1170. [α]$_D$ (CHCl$_3$, C=5.035 mg/ml)-19°. Recrystallized from EtOAc-hexane: m.p. 113.0°–116.1°. C, H, N calcd for C$_{18}$H$_3$#1NO$_5$F$_2$: C, 56.98; H, 8.23; N, 3.69; F, 10.01. Found: C, 57.37; H, 8.15; N, 3.71.

Minor isomer: $^1$H-NMR (CDCl$_3$): δ 1.37, 1.45, and 4.34. IR (neat) 3425, 2925, 1760, 1695, 1510, and 1170. [α]$_D$—40°. Recrystallized from EtOAc-hexane: m.p. 72.8°–74.5°. Anal. calcd. for C$_{18}$H$_{31}$NO$_5$F$_2$: C, 56.98; H, 8.23; N, 3.69; F, 10.01. Found: C, 57.19; H, 8.60; N, 3.52.

EXAMPLE 1

Ethyl-4S-tert-butyloxycarbonylamino-2,2-difluoro-3R-hydroxy-6-methylheptanoate A-1

Refer to Chart A, Step 1

To a stirred suspension of 810 mg (12.4 mmol) of activated zinc dust in 4 ml of tetrahydrofuran in an oil bath at 75° C. under argon was added a solution of 400 mg (2.0 mmol) of ethyl bromodifluoroacetate in 1 ml of tetrahydrofuran. After 2 min, a solution of 2.0 g (10 mmol) of ethyl bromodifluoroacetate and 1.07 g (4.97 mmol) of Boc-L-leucinal in 4 ml of tetrahydrofuran was slowly added withh 1 ml of tetrahydrofuran rinse. After heating for an additional 30 min, the reaction mixture was allowed to cool. It was then added to 30 ml of 1M aqueous potassium disulfate (KHSO$_4$). Tetrahydrofuran was removed on a rotary evaporator. The aqueous phase was extracted with four 50 ml portions of dichloromethane. The combined organic phase was dried over magnesium sulfate (MgSO$_4$), filtered, and then concentrated. The resulting residue was chromatographed on silica gel with 15% ethyl acetate in hexane, to give 950 mg (2.8 mmol, 56%) of compound A-1, $^1$H-NMR (CDCl$_3$): δ 0.97, 1.38, 1.47, 4.3. IR: 3390, 1760, 1690; MS: m/z=266, 238, 186, 130, 86; Anal. Calc'd. for C$_{15}$H$_{27}$NO$_5$F$_2$: C, 53.12; H, 7.96; N, 4.12. Found: C, 53.37; H, 8.14; N, 4.01.

EXAMPLE 2

Sodium-4S-tert-butyloxycarbonylamino-2,2-difluoro-3R-hydroxy-6-methyl-heptanoate A-2

Refer to Chart A, Step 2

To a stirred solution of 394.4 mg (1.16 mmol) of the ester A-1 in 2.4 ml of tetrahydrofuran was added 1.2 ml (1.2 mmol) of a 1.0M aqueous sodium hydroxide (NaOH) solution. After 2 hr, tetrahydrofuran was removed by a stream of nitrogen. The remaining aqueous phase was diluted with 2 ml of water and the resulting solution lyophilized to the titled white solid.

EXAMPLE 3

N-tert-Butyloxycarbonyl-2,2-difluoro-statyl-L-isoleucyl-2-pyridylmethylamide A-3

Refer to Chart A, Step 3

To a stirred solution of 1.16 mmol of the sodium salt A-2, 385 mg (1.74 mmol) of L-isoleucyl-2-pyridylmethylamide, and 361 mg (2.67 mmol) of 1-hydroxy-benzotriazole in 6 ml of dichloromethane was added 311 mg (1.51 mmol) of diclohexylcarbodiimide. After 2 days, the reaction mixture was partitioned between 50 ml of dichloromethane and 30 ml of saturated aqueous sodium bicarbonate (NaHCO$_3$). The aqueous phase was extracted with three 30 ml portions of dichloromethane. The combined organic phase was dried over magnesium sulfate (MgSO$_4$), filtered, and then concentrated. The residue was triturated with ethyl acetate and then filtered. The concentrated filtrate was chromatographed on silica gel with 60% ethyl acetate in hexane to give 444 mg (0.86 mmol, 74%) of peptide A-3, structure of which was supported by $^1$H-NMR and MS (FAB): m/z=514.

EXAMPLE 4

N-tert-Butyloxycarbonyl-N-$^{im}$-tosyl-L-histidyl-2,2-difluoro-statyl-L-isoleucyl-2-pyridyl-methylamide A-4

Refer to Chart A, Step 4

To a stirred solution of 0.305 mmol of the peptide (from treatment of peptide A-3 with 1:1=trifluoroacetic acid:dichloromethane and then neutralization with aqueous NaHCO$_3$), 156 mg (0.38 mmol) of Boc-His(Ts) and 60 μl (0.43 mmol) of triethylamine in 2 ml of dichloromethane was added 60 μl (0.39 mmol) of diethylphosphoryl cyanide. After 15 hr, the reaction mixture was partitioned between 20 ml of dichloromethane and 20 ml of saturated aqueous NaHCO$_3$. The aqueous phase was extracted with three 15 ml portions of dichloromethane. The combined organic phase was dried (MgSO$_4$), filtered, and then concentrated. The resulting residue was chromatographed on silica gel with 70% ethyl acetate in hexane to give 220 mg (0.273 mmol, 90%) of peptide A-4, structure of which was supported by $^1$H-NMR.

EXAMPLE 5

N-tert-Butyloxycarbonyl-L-phenylalanyl-N$^{im}$-tosyl-L-histidyl-2,2-difluoro-statyl-L-isoleucyl-2-pyridylmethylamide A-5

Refer to Chart A, Step 5

To a stirred solution of 0.273 mmol of the peptide (from treatment of peptide A-4 with 1:1=trifluoroacetic acid:dichloromethane and then neutralization with aqueous NaHCO$_3$), 90 mg (0.34 mmol) of Boc-Phe and 60 μl (0.43 mmol) of triethylamine in 2 ml of dichloromethane was added 60 μl (0.39 mmol) of diethylphosphoryl cyanide. After 24 hr, the reaction mixture was partitioned between 20 ml of dichloromethane and 20 ml of saturated aqueous NaHCO$_3$. The aqueous phase was extracted with three 15 ml portions of dichloromethane. The combined organic phase was dried (MgSO$_4$), filtered, and then concentrated. It was passed through silica gel with tetrahydrofuran loading and ethyl acetate elusion to give 162 mg (0.17 mmol, 62%) of peptide A-5, structure of which was supported by $^1$H-NMR.

EXAMPLE 6

N-tert-Butyloxycarbonyl-L-phenylalanyl-L-histidyl-2,2-difluoro-statyl-L-isoleucyl-2-pyridylmethylamide A-6

Refer to Chart A, Step 6

To a solution of 15 mg (0.016 mmol) of the peptide A-5 in 0.5 ml of methanol was added 30 mg (0.22 mmol) of 1-hydroxy-benzotriazole. After 14 hr, the reaction mixture was concentrated and the residue chromatographed on silica gel with 5% methanol (saturated with ammonia) in ethyl acetate to give 9 mg of peptide VI, structure of which was supported by $^1$H-NMR and MS (FAB): [M+H]$^+$ at m/z=799.4305.

EXAMPLE 7

N-tert-Butyloxycarbonyl-L-phenylalanyl-N$^{im}$-tosyl-L-histidyl-2,2-difluoro-statonyl-L-isoleucyl-2-pyridylmethylamide A-5a Refer to Chart A, Step 5a To a stirred solution of 25 μl (287 mmol) of oxalyl chloride in 0.5 ml of dichloromethane at −78° C. was added 40 μl (564 mmol) of dimethylsulfoxide. After 10 min, this solution was added to a stirred solution of 162 mg (0.17 mmol) of peptide of Example 5 in 0.5 ml of dimethylsulfoxide. The resulting mixture was allowed to stir in an ice bath for 15 min, and then 80 μl (574 mmol) of triethylamine was added. After 5 min, the reaction mixture was partitioned between 20 ml of dichloromethane and 20 ml of saturated aqueous NaHCO$_3$. The aqueous phase was extracted with three 15 ml portions of dichloromethane. The combined organic phase was dried (MgSO$_4$), filtered, and then concentrated. The resulting residue was chromatographed on silica gel with 80% ethyl acetate in hexane to give 77 mg (0.08 mmol, 48%) of peptide A-5a.

EXAMPLE 8

N-tert-Butyloxycarbonyl-L-phenylalanyl-L-histidyl-2,2-difluoro-statonyl-L-isoleucyl-2-pyridylmethylamide A-6a Refer to Chart A, step 6a To a stirred solution of 77 mg (0.08 mmol) of the peptide A-5a in 1 ml of methanol was added 50 mg (0.37 mmol) of 1-hydroxy-benzotriazole. After 10 hr, the reaction mixture was concentrated and the resulting residue chromatographed on silica gel with 5% methanol (saturated with ammonia) in ethyl acetate to give 30 mg of the peptide A-6a, structure of which was supported by $^1$H-NMR (HPLC indicated mixture of diastereomers) and MS (FAB): [M+H]$^+$ at m/z=797.4193 and 10 mg of the corresponding alcohol (A-6a) due to incomplete oxidation of the previous reaction).

EXAMPLE 9

In like manner, the following isomeric mixtures are prepared:

N-tert-butyloxycarbonyl-L-phenylalanyl-L-histidyl-4S-amino-2,2-difluoro-3R-hydroxy-4-phenylmethyl-1-oxobutyl-L-isoleucyl-2-pyridylmethyl-amide;

N-tert-butyloxycarbonyl-L-phenylalanyl-L-histidyl-4S-amino-4-cyclohexylmethyl-2,2-difluoro-3R-hydroxy-1-oxobutyl-L-isoleucyl-2-pyridylmethylamide;

N-tert-butyloxycarbonyl-L-phenylalanyl-L-histidyl-4-amino-2,2-difluoro-3-hydroxy-4-phenylmethyl-1-oxobutyl-L-isoleucyl-2-pyridylmethylamide (mixture of three isomers);

N-tert-butyloxycarbonyl-L-phenylalanyl-L-histidyl-4-amino-4-cyclohexylmethyl-2,2-difluoro-3-hydroxy-1-oxobutyl-1-isoleucyl-2-pyridylmethylamide (mixture of three isomers);

N-tert-butyloxycarbonyl-L-phenylalanyl-L-histidyl-4-amino-2,2-difluoro-4-phenylmethyl-1,3-dioxobutyl-L-isoleucyl-2-pyridylmethylamide; and N-tert-butyloxycarbonyl-L-phenylalanyl-L-histidyl-4-amino-4-cyclohexylmethyl-2,2-difluoro-1,3-dioxobutyl-L-isoleucyl-2-pyridylmethylamide.

Table I shows the molecular weight, using mass spectroscopy, and elution times, using HPLC, of these isomers. Note that the compound containing moieties X and XI are pure isomers. In Table I, the number of the HPLC retention times given for a particular entry indicates the number of isomers represented by that entry.

EXAMPLE 10

Following the procedures of the preceding Examples, the following compounds are prepared:

Ac—Trp(CHO)—Pro—Phe—His—Sta$^{2f}$—Ile—AMP

Ac—Trp(CHO)—Pro—Phe—His—Sto$^{2f}$—Ile—AMP

Ac—Pro—Phe—His—Sta$^{2f}$—Ile—AMP

Ac—Pro—Phe—His—Sto$^{2f}$—Ile—AMP

Ac—Trp(CHO)—Pro—Phe—N—Me—His—Sta$^{2f}$—Ile—AMP

Ac—Trp(CHO)—Pro—Phe—N—Me—His—Sto$^{2f}$—Ile—AMP

Ac—Pro—Phe—N—Me—His—Sta$^{2f}$—Ile—AMP

Ac—Pro—Phe—N—Me—His—Sto$^{2f}$—Ile—AMP

Ac—Pla—His—Sta$^{2f}$—Ile—AMP

Ac—Pla—His—Sto$^{2f}$—Ile—AMP

Ac—Nla—His—Sta$^{2f}$—Ile—AMP

Ac—Nla—His—Sto$^{2f}$—Ile—AMP

NOA—His—Sta$^{2f}$—Ile—AMP

NOA—His—Sto$^{2f}$—Ile—AMP

Also prepared are each of the above compounds wherein the —Ile— moiety is absent.

Also prepared are each of the above compounds wherein the AMP is replaced by isobutylamino or benzylamino.

Also prepared are each of the above compounds wherein the Sta$^{2f}$ is replaced by the moiety —(X)— or —(XI)—; and wherein Sto2f is replaced by the moiety (XIV) or (XV).

Table II depicts compounds of the present invention, prepared by the methods described above, in relation to the renin substrate "Abs" means the moiety is absent.

TABLE I

| | HPLC[1] | MS[2] |
|---|---|---|
| Boc—Phe—His—(X)-Ile—AMP | 12.3 | 833.4174 |
| Boc—Phe—His—(XI)-Ile—AMP | 15.2 | 839.4607 |
| Boc—Phe—His—(XII)-Ile—AMP | 10.9, 11.5, 13.0 | 833 |
| Boc—Phe—His—(XIII)-Ile—AMP | 12.3, 14.3, 16.0 | 839 |
| Boc—Phe—His—(XIV)-Ile—AMP | 11.6, 12.6 | 831.4016 |
| Boc—Phe—His—(XV)-Ile—AMP | 13.2, 16.2 | 837.4474 |
| Boc—Phe—His—(XV)-Ile—AMP, Isomer A | 11.4 | 837.4465 |
| Boc—Phe—His—(XV)-Ile—AMP, Isomer B | 14.8 | 837.4482 |

X                    XI

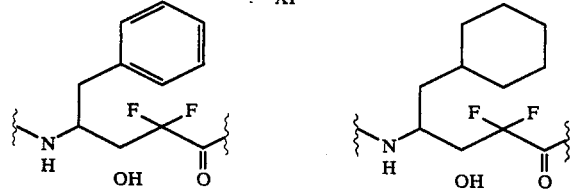

XII                  XIII

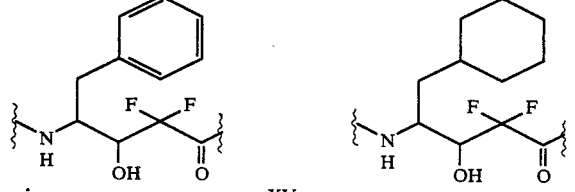

XIV                  XV

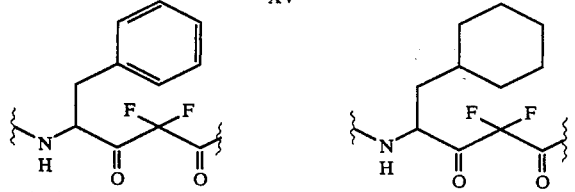

[1] HPLC retention in minutes with detector set at 254 nm, and eluting with 90% methanol, 10% aqueous phosphate buffer (pH 3), on a 10 micron reverse-phase column, flow rate 1.5 mL/min.
[2] FAB MS: [M + H]+ at m/z.

FORMULAS

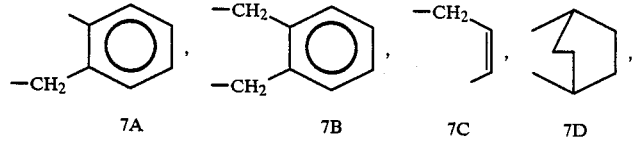

7A        7B        7C        7D

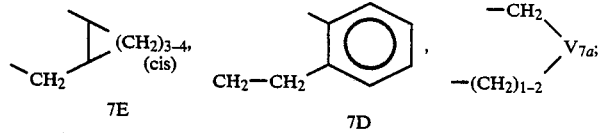

7E        7D

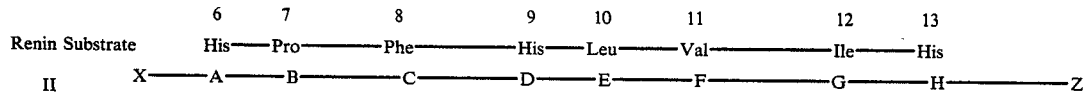

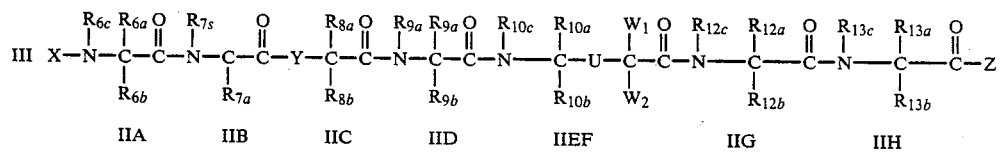

CHART A
Scheme I

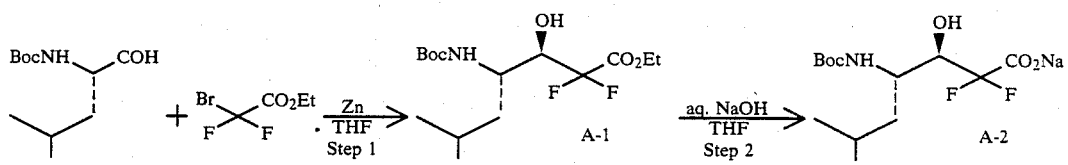
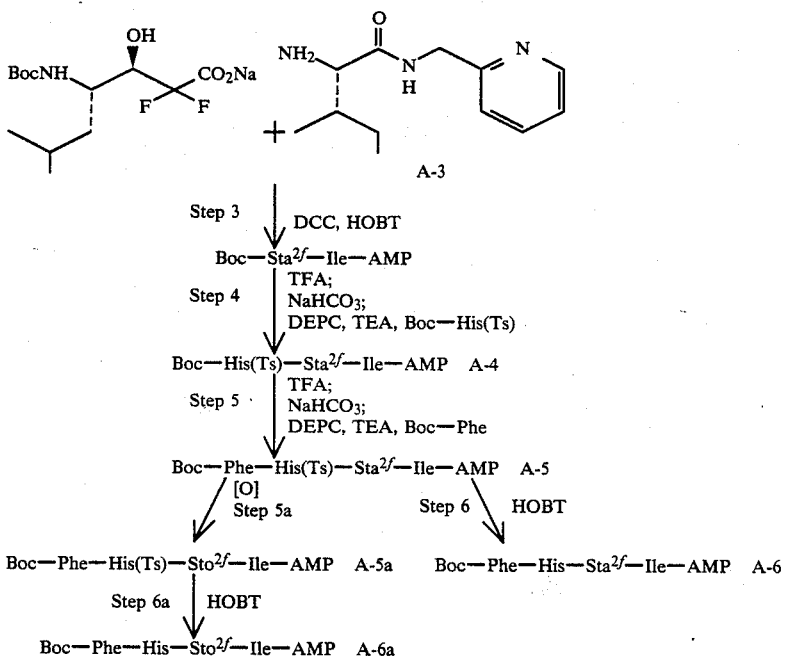
CHART B
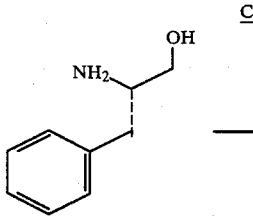
I
B-1
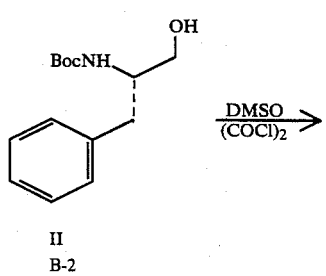
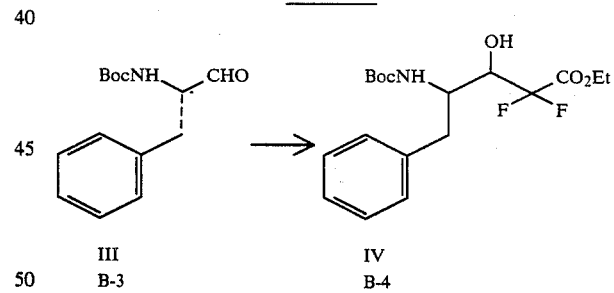
III          IV
B-3         B-4
TABLE II
| Cpd # | 6 His | 7 Pro | 8 Phe | 9 His | 10 Leu | 11 Val | 12 Ile | 13 His | HPLC[1] time/ (min) | FAB MS (found) |
|---|---|---|---|---|---|---|---|---|---|---|
|  |  |  | X — A — B — C — D — E — F — G — H — Z |  |  |  |  |  |  |  |
| 1 | Boc | abs | abs | Phe | His | AHPPA2f | Ile | abs | AMP | See examples |
| 2 | Boc | abs | abs | Phe | His | ACHPA2f | Ile | abs | AMP | See examples |
| 3 | Boc | abs | abs | Phe | His | AHPPA2f3 | Ile | abs | AMP | See examples |

TABLE II-continued

| Cpd # | 6 His | 7 Pro | 8 Phe | 9 His | 10 Leu | 11 Val | 12 Ile | 13 His | HPLC[1] time/ (min) | FAB MS (found) |
|---|---|---|---|---|---|---|---|---|---|---|
| 4 | Boc | abs | abs | Phe | His | ACHPA2f3 | Ile | abs | AMP | See examples |
| 5 | Boc | abs | abs | Phe | His | AOPPA2f | Ile | abs | AMP | See examples |
| 6 | Boc | abs | abs | Phe | His | ACOPA2f | Ile | abs | AMP | See examples |
| 7 | Boc | abs | abs | Phe | His | ACHPA2f | Ile | abs | AMP | See examples |
| 8 | Boc | abs | abs | Phe | His | ACOPA2f | Ile | abs | AMP | See examples |
| 9 | Boc | abs | abs | Phe | His | Sta$^{2f}$ | Ile | abs | AMP | 12.6 | 799.430 |
| 10 | Boc | abs | abs | Phe | NMHis | ACHPA$^{2f}$ | Ile | abs | AMP | 11.6 | 853.4799 |
| 11 | Boc | abs | Pro | Phe | NMHis | ACHPA$^{2}_{f}$ | Ile | abs | AMP | 14.1 | 950.5313 |
| 12 | 1NOAc | abs | abs | abs | His | ACHPA2f | Ile | abs | AMP | 10.4 | 776.3965 |
| 13 | Ac | FTrp | Pro | Phe | NMHis | ACHPA2f | Ile | abs | AMP | 12.3 | 1144.5189 |
| 14 | Boc | abs | abs | Phe | His | ACHPA2f | abs | abs | MBA2S | 10.3 | 705.4128 |
| 15 | Boc | abs | abs | Phe | His | ACHPA2f | abs | abs | MBA3 | 10.5 | 705.4156 |
| 16 | Ac | NLA1S | abs | abs | His | ACHPA2f | Ile | abs | AMP | 12.3 | 832.4195 |
| 17 | Boc | aba | abs | Phe | His | Sto$^{2f}$ | Ile | abs | AMP | 9.9 | 797.4161 |
| 18 | Boc | abs | abs | Phe | His | Sto$^{2f}$ | Ile | abs | AMP | 11.2 | 797.4169 |
| 19 | Boc | abs | abs | Phe | NMHis | ACOPA2f | Ile | abs | AMP | 11.5 13.3 | 851.4607 |
| 20 | Boc | abs | Pro | Phe | NMHis | ACOPA2f | Ile | abs | AMP | 12.1 15.0 | 948.5127 |
| 21 | 1NOAc | abs | abs | abs | His | ACOPA2f | Ile | abs | AMP | 8.8 11.0 | 774.3772 |
| 22 | Boc | abs | abs | Phe | His | ACOPA2f | abs | abs | MBA2s | 9.8 11.6 | 703.4011 |
| 23 | Ac | NLA1S | abs | abs | His | ACOPA2f | Ile | abs | AMP | 11.3 13.7 | 830.4052 |
| 24 | Boc | abs | abs | Phe | His | ACOPA2f | abs | abs | MBA3 | 9.9 11.7 | 703.3990 |

[1]Conditions are as in Table I.

I claim:

1. A renin inhibitory peptide of the formula II, shown in relation to the renin substrate as follows:

Renin Substrate

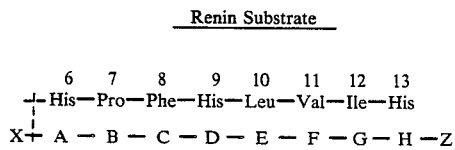

wherein X is
(a) hydrogen,
(b) $R_{x1}$—,
(c) $R_{x1}$—$V_{x1}$—$C(R_{x2})(R_{x3})CO$—,
(d) $R_{x4}$—$N(R_{x4})(CH_2)_{0-6}$—$CO$—,
(e) $R_{x5}$—$O$—$CO$—$(CH_2)_{1-6}$—$CO$—,
(f) $R_{x5}$—$N$—$(R_{x5})$—$CO$—$(CH_2)_{1-6}$—$CO$—,
(g) $R_{x4}$—$SO_2$—$N(R_{x5})(CH_2)_{1-6}$—$CO$—,
(h) $R_{x4}$—$N(R_{x4})(CH_2)_{0-6}$—$SO_2$—$(CH_2)_{1-6}$—$CO$—,
(i) Arg—,
(j) Arg—Arg—,
(k) $R_{x6}$—$O$—$CH_2$—$CO$—,
(l) $R_{x6}$—$CH_2$—$O$—$CO$—,
(m) $R_{x6}$—$O$—$CO$—, or
(n) $R_{x6}$—$(CH_2)_{0-6}$—$CO$—;

wherein —A— is absent or a divalent moiety of the formula IIA;

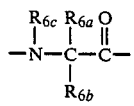

wherein —B— is absent or a divalent moiety of the formula IIB;

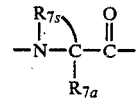

wherein —C— is absent or a divalent moiety of the formula IIC;

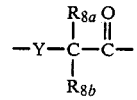

wherein —D— is a divalent moiety of the formula IID;

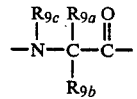

wherein —E—F— is a divalent moiety of the formula IIEF;

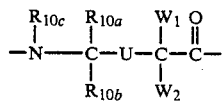

wherein —G— is absent or a divalent moiety of the formula IIG;

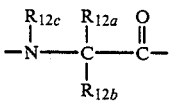

wherein —H— is absent or a divalent moiety of the formula IIH;

$$-N(R_{13c})-C(R_{13a})(R_{13b})-C(=O)-$$

wherein Z is
- (a) $-V_{z1}-(CH_2)_{0-6}-R_{z1}$,
- (b) $-V_{z1}-CH_2-(C_1-C_5 hydroxyalkyl)$,
- (c) $-V_{z1}-CH_2-(C_1-C_5 aminoalkyl)$,
- (d) $-V_{z1}-CH_2-((C_1-C_5 alkyl)-(mono-, di-, or tri-C_{1-C_5}alkyl)amino$,
- (e) $-V_{z1}-CH_2-((C_1-C_5 alkyl)-guanidyl)$,
- (f) d or l—Lys—OH,
- (g) d or l—Lys—NH$_2$,
- (h) d or l—Ser—OH, or
- (i) d or l—Ser—NH$_2$;

wherein Y is $-N(R_{8c})-$, or divalent oxygen (—O—); with the provisos that
(1) when Y is absent or $-N(R_{8c})-$, X is
- (a) hydrogen,
- (b) $R_{x1}-$,
- (c) $R_{x1}-V_{x1}-C(R_{x2})(R_{x3})CO-$,
- (d) $R_{x4}-N(R_{x4})(CH_2)_{0-6}-CO-$,
- (e) $R_{x5}-O-CO-(CH_2)_{1-6}-CO-$,
- (f) $R_{x5}-N-(R_{x5})-CO-(CH_2)_{1-6}-CO-$,
- (g) $R_{x4}-SO_2-N(R_{x5})(CH_2)_{1-6}-CO-$,
- (h) $R_{x4}-N(R_{x4})(CH_2)_{0-6}-SO_2-(CH_2)_{1-6}-CO-$,
- (i) Arg—, or
- (j) Arg—Arg—; and (2) when Y is —O—, A and B are both absent and X is
- (a) hydrogen,
- (b) $R_{x6}-O-CH_2-CO-$,
- (c) $R_{x6}-CH_2-O-CO-$,
- (d) $R_{x6}-O-CO-$,
- (e) $R_{x6}-(CH_2)_{0-6}-CO-$, or
- (f) $R_{x5}-N(R_{x5})-CH_2-CO-$;

wherein —U— is
- (a) —C(O)—,
- (b) —CH(OH)—, or
- (c) —CH(NH$_2$)—;

wherein W$_1$ and W$_2$ are the same or different and are
- (a) fluoro,
- (b) chloro,
- (c) bromo, or
- (d) hydrogen with the proviso that W$_1$ and W$_2$ are not hydrogen simultaneously;

wherein R$_{x1}$ is
- (a) $R_{x4}-(CH_2)_{0-2}-$,
- (b) $R_{x4}-CO-$,
- (c) $R_{x4}-(CH_2)_{0-5}-O-CO$, wherein $R_{x4}$ is not hydrogen,
- (d) $R_{x4}-(CH_2)_{1-5}-CO-$,
- (e) $R_{x4}-(CH_2)_{0-4}-SO_2-$,
- (f) $R_{x4}-SO_2-(CH_2)_{0-4}-$, with the proviso that $X_{x1}$ is other than oxygen for (CH$_2$)$_0$, or
- (g) $R_{x4}-SO_2-(CH_2)_{2-4}-O-CO-$;

wherein R$_{x2}$ is
- (a) hydrogen,
- (b) C$_1$-C$_8$alkyl,
- (c) C$_3$-C$_7$cycloalkyl,
- (d) aryl,
- (e) heterocycle,
- (f) $-CH(R_{x3})-$aryl,
- (g) $-CH(R_{x3})-$heterocycle;
- (h) $-CH_2CH_2-$aryl,
- (i) $-CH_2CH_2-$heterocycle,
- (j) —OH,
- (k) $-CH(R_{x3})-$OH,
- (l) $-CH(R_{x3})-$SH,
- (m) $-CH(R_{x3})-$OCH$_3$, or
- (n) $-CH(R_{x3})-$SCH$_3$;

wherein R$_{x3}$ is
- (a) hydrogen or
- (b) C$_1$-C$_3$alkyl;

wherein R$_{x4}$ is
- (a) hydrogen,
- (b) C$_1$-C$_7$alkyl,
- (c) C$_3$-C$_7$cycloalkyl,
- (d) $-CH_2-(C_1-C_4 hydroxyalkyl)$,
- (e) $-CH_2-(C_1-C_4 aminoalkyl)$,
- (f) aryl or
- (g) heterocycle;

wherein R$_{x5}$ is
- (a) hydrogen or
- (b) C$_1$-C$_6$alkyl;

wherein R$_{x6}$ is
- (a) C$_1$-C$_6$alkyl,
- (b) C$_3$-C$_7$alkyl,
- (c) aryl, or
- (d) heterocycle;

wherein R$_{6a}$ is
- (a) hydrogen, or
- (b) C$_1$-C$_3$alkyl;

wherein R$_{6b}$ is $-[CH(R_{6e})]_{0-3}-R_{6f}$;

wherein R$_{6c}$ is
- (a) hydrogen, or
- (b) C$_1$-C$_3$alkyl;

wherein R$_{6e}$ is
- (a) hydrogen, or
- (b) C$_1$-C$_3$alkyl;

wherein R$_{6f}$ is
- (a) hydroxy,
- (b) C$_1$-C$_6$alkyl,
- (c) C$_3$-C$_{10}$cycloalkyl,
- (d) aryl,
- (e) heterocycle,
- (f) $-(CH_2)_{0-3}-$SH,
- (g) C$_7$-C$_{14}$bi- or tricycloalkyl,
- (h) C$_1$-C$_4$hydroxyalkyl,
- (i) C$_1$-C$_3$alkyloxy,
- (j) C$_1$-C$_3$alkyloxy—(C$_1$-C$_4$alkyl)—,
- (k) aryl—O—,
- (l) aryl—O—(C$_1$-C$_4$alkyl)-,
- (m) aryl—CH$_2$—O—, or
- (n) aryl—CH$_2$—O—(C$_1$-C$_4$alkyl)—;

wherein R$_{7a}$ is
- (a) hydrogen, or
- (b) C$_1$-C$_3$alkyl;

wherein R$_{7s}$ is
- (a) $-(CH_2)_3-$, or
- (b) a divalent substituent of the formula 7A, 7B, 7C, 7D, 7E, 7F, or 7G;

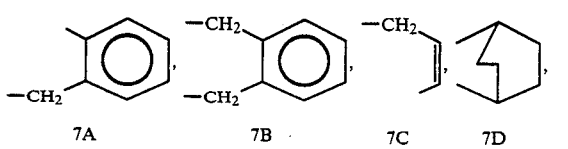

7A    7B    7C    7D

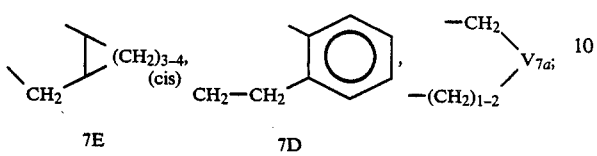

7E    7D wherein $R_{8a}$ is
- (a) hydrogen, or
- (b) $C_1$–$C_3$alkyl;

wherein $R_{8b}$ is —$[CH(R_{6e})]_{0-3}$—$R_{6f}$;

wherein $R_{8c}$ is
- (a) hydrogen, or
- (b) $C_1$–$C_3$alkyl;

wherein $R_{9a}$ is
- (a) hydrogen, or
- (b) $C_1$–$C_3$alkyl;

wherein $R_{9b}$ is —$[CH(R_{9e})]_{0-3}$—$R_{9f}$;

wherein $R_{9c}$ is
- (a) hydrogen, or
- (b) $C_1$–$C_3$alkyl;

wherein $R_{9e}$ is
- (a) hydrogen, or
- (b) $C_1$–$C_3$alkyl;

wherein $R_{9f}$ is
- (a) hydrogen,
- (b) aryl,
- (c) heterocycle,
- (d) $C_1$–$C_6$alkyl,
- (e) $C_3$–$C_{10}$cycloalkyl,
- (f) $C_7$–$C_{14}$bi- or tricycloalkyl,
- (g) —$NH_2$,
- (h) —OH,
- (i) $C_1$–$C_4$aminoalkyl,
- (j) $C_1$–$C_4$hydroxyalkyl,
- (k) $C_1$–$C_3$alkyloxy—($C_1$–$C_4$alkyl)—
- (l) —$(CH_2)_{1-6}$—$NHC(=NH)NH_2$,
- (m) —$CH_2SCH_3$,
- (n) —$(CH_2)_{0-4}CO$—$R_{9d}$,
- (o) —O—aryl,
- (p) —O—$CH_2$—aryl,
- (q) —($C_1$–$C_4$alkyl)—O—aryl,
- (r) —($C_1$–$C_4$alkyl)—O—$CH_2$—aryl,
- (s) —O—$CH_2$—heterocycle, or
- (t) —($C_1$–$C_4$alkyl)—O—$CH_2$—heterocycle;

wherein $R_{9d}$ is
- (a) hydrogen,
- (b) $NH_2$, or
- (c) $C_1$–$C_3$alkyloxy;

wherein $R_{10a}$ is
- (a) hydrogen, or
- (b) $C_1$–$C_3$alkyl;

wherein $R_{10b}$ is
- (a) $C_1$–$C_7$alkyl,
- (b) $C_3$–$C_7$cycloalkyl,
- (c) —$(CH_2)_{1-4}$—($C_3$–$C_7$cycloalkyl),
- (d) —$(CH_2)_{1-4}$—aryl,
- (e) —$(CH_2)_{1-4}$—heterocycle,
- (f) $C_5$–$C_7$cycloalkenyl, or
- (g) —$(CH_2)_{1-4}$—($C_5$–$C_7$cycloalkenyl);

wherein $R_{10c}$ is
- (a) hydrogen, or
- (b) $C_1$–$C_3$alkyl;

wherein $R_{12a}$ is
- (a) hydrogen, or
- (b) $C_1$–$C_3$alkyl;

wherein $R_{12b}$ is
- (a) hydrogen, or
- (b) —$[CH(R_{12e})]_{0-4}$—$R_{12f}$;

wherein $R_{12c}$ is
- (a) hydrogen, or
- (b) $C_1$–$C_3$alkyl;

wherein $R_{12e}$ is
- (a) hydrogen, or
- (b) $C_1$–$C_3$alkyl;

wherein $R_{12f}$ is
- (a) hydrogen,
- (b) aryl,
- (c) heterocycle,
- (d) $C_1$–$C_6$alkyl,
- (e) $C_3$–$C_{10}$cycloalkyl, or
- (f) $C_7$–$C_{14}$bi- or tricycloalkyl;
- (g) hydroxy,
- (h) $C_1$–$C_4$hydroxyalkyl,
- (i) $C_1$–$C_3$alkyloxy,
- (j) $C_1$–$C_3$alkyloxy—($C_1$–$C_4$alkyl)—,
- (k) aryl—O—,
- (l) aryl—O—($C_1$–$C_4$alkyl)—,
- (m) aryl—$CH_2$—O—, or
- (n) aryl—$CH_2$—O—($C_1$–$C_4$alkyl)—;

wherein $R_{13a}$ is
- (a) hydrogen, or
- (b) $C_1$–$C_3$alkyl;

wherein $R_{13b}$ is —$[CH(R_{13e})]_{0-4}$—$R_{13f}$;

wherein $R_{13c}$ is
- (a) hydrogen, or
- (b) $C_1$–$C_3$alkyl;

wherein $R_{13e}$ is
- (a) hydrogen, or
- (b) $C_1$–$C_3$alkyl;

wherein $R_{13f}$ is
- (a) hydrogen,
- (b) aryl,
- (c) heterocycle,
- (d) $C_1$–$C_6$alkyl
- (e) $C_3$–$C_{10}$cycloalkyl,
- (f) $C_7$–$C_{14}$bi- or tricycloalkyl,
- (g) hydroxy,
- (h) amino,
- (i) $C_1$–$C_4$aminoalkyl,
- (j) $C_1$–$C_4$hydroxyalkyl,
- (k) $C_1$–$C_3$alkyloxy,
- (l) $C_1$–$C_3$alkyloxy—($C_1$–$C_4$alkyl)—,
- (m) —$(CH_2)_{1-6}$—$NHGC(=NH)NH_2$,
- (n) —$CH_2SCH_3$,
- (o) —$(CH_2)_{0-4}$—CO—$R_{13g}$,
- (p) aryl—O—,
- (q) aryl—O—($C_1$–$C_4$alkyl)—
- (r) aryl—$CH_2$—O—,
- (s) aryl—$CH_2$—O—($C_1$–$C_4$alkyl)—
- (t) heterocycle—$CH_2$—O—, or
- (u) heterocycle—$CH_2$—O—($C_1$–$C_4$alkyl)—;

wherein $R_{13g}$ is
- (a) OH,
- (b) $NH_2$, or
- (c) $C_1$–$C_3$alkyloxy;

wherein $R_{z1}$ is
- (a) hydrogen, (b) C₁–C₇ alkyl,
(c) C₃–C₇cycloalkyl,
(d) aryl, or
(e) heterocycle; and
wherein R$_{z2}$ is
(a) hydrogen, or
(b) C₁–C₃alkyl;
wherein V$_{x1}$ is
(a) —CH₂—,
(b) —CH(R$_{x1}$),
(c) —N(R$_{x5}$)—,
(d) —O—;
(e) —S—,
(f) —SO—, or
(g) —SO₂—;
wherein V$_{z1}$ is
(a) —O—,
(b) —S—, or
(c) —N(R$_{z2}$)—;
wherein V$_{7a}$ is
(a) —O—,
(b) —S—, or
(c) —CH(OH)—.

2. A compound of claim 1,
wherein X is
(a) hydrogen,
(b) CH₃CO—,
(c) (CH₃)₃C—O—CO—, or
(d) (CH₃)₃C—CH₂—CO—;
wherein R$_{6a}$ and R$_{6c}$ are hydrogen;
wherein R$_{6b}$ is
(a) benzyl,
(b) (2-naphthyl)methyl,
(c) N$^{in}$-formylindole-3-methyl-,
(d) -1H-imidazole-4-methyl-, or
(e) (1-naphthyl-)methyl-
wherein R$_{7s}$ is —(CH₂)₃—;
wherein R$_{7a}$ is
(a) hydrogen, or
(b) CH₃;
wherein R$_{8a}$ and R$_{8c}$ are hydrogen;
wherein R$_{8b}$ is
(a) benzyl,
(b) (2-naphthyl)methyl,
(c) N$^{in}$-formylindole-3-methyl, or
(d) (1-naphthyl-)methyl;
wherein R$_{9c}$ is hydrogen, or CH₃;
wherein R$_{9a}$ is hydrogen;
wherein R$_{9b}$ is
(a) benzyl,
(b) p-chloro-benzyl,
(c) -imidazole-4-methyl-,
(c) (2-, 3-, or 4-pyridinyl)-methyl-, or
(e) C₁–C₃alkyl;
wherein R$_{10a}$ and R$_{10c}$ are hydrogen;
wherein R$_{10b}$ is
(a) 2-methylpropyl,
(b) benzyl, or
(c) cyclohexylmethyl;
wherein W₁ and W₂ are fluorine;
wherein —G— is a divalent moiety of the formula IIG;
wherein R$_{12a}$ and R$_{12c}$ are hydrogen;
wherein R$_{12b}$ is
(a) hydrogen,
(b) —CH₃,
(c) —CH₂CH₃,
(d) —CH(CH₃)₂,
(e) —CH₂CH(CH₃)₂ or
(f) —CH(CH₃)CH₂CH₃;
wherein —H— is absent;
wherein —Z— is
(a) OH,
(b) NH₂,
(c) phenyl-(C₁–C₃alkyl)-amino-,
(d) (2-, 3-, or 4-pyridinyl)-(C₁–C₃-alkylamino-, or
(e) C₁–C₆alkyl-amino-;
and chiral centers are of the S or analogous configuration.

3. A compound of claim 2 wherein R$_{15}$ is t-butoxycarbonyl, R$_{14}$ is ethyl or sodium, R$_{10b}$ is isobutyl, benzyl or cyclohexylmethyl, and R$_{10a}$ and R$_{10c}$ are hydrogen.

4. N-tert-butyloxycarbonyl-L-phenylalanyl-L-histidyl-4S-amino-2,2-difluoro-3R-hydroxy-4-phenylmethyl-1-oxobutyl-L-isoleucyl-2-pyridylmethylamide;
N-tert-butyloxycarbonyl-L-phenylalanyl-L-histidyl-4S-amino-4-cyclohexylmethyl-2,2-difluoro-3R-hydroxy-1-oxobutyl-L-isoleucyl-2-pyridylmethylamide;
N-tert-butyloxycarbonyl-L-phenylalanyl-L-histidyl-4-amino-2,2-difluoro-3-hydroxy-4-phenylmethyl-1-oxobutyl-L-isoleucyl-2-pyridylmethylamide (mixture of three isomers);
N-tert-butyloxycarbonyl-L-phenylalanyl-L-histidyl-4-amino-4-cyclohexylmethyl-2,2-difluoro-3-hydroxy-1-oxobutyl-L-isoleucyl-2-pyridylmethylamide (mixture of three isomers);
N-tert-butyloxycarbonyl-L-phenylalanyl-L-histidyl-4-amino-2,2-difluoro-4-phenylmethyl-1,3-dioxobutyl-L-isoleucyl-2-pyridylmethylamide; and
N-tert-butyloxycarbonyl-L-phenylalanyl-L-histidyl-4-amino-4-cyclohexylmethyl-2,2-difluoro-1,3-dioxobutyl-L-isoleucyl-2-pyridylmethylamide; compounds of claim 2.

5. A compound of claim 2, N-tert-butyloxycarbonyl-L-phenylalanyl-L-histidyl-4S-amino-2,2-difluoro-3R-hydroxy-4-(2-methylpropyl)-1-oxobutyl-L-isoleucyl-2-pyridylmethylamide.

6. A compound of claim 2, N-tert-butyloxycarbonyl-L-phenylalanyl-L-histidyl-4-amino-2,2-difluoro-4-(2-methylpropyl)-1,3-dioxobutyl-L-isoleucyl-2-pyridylmethylamide.

7. A compound of claim 2, selected from the group consisting of:

Boc—Phe—His—Sta$^{2f}$—Ile—AMP;

Boc—Phe—NMHis—ACHPA2f—Ile—AMP;

Boc—Pro—Phe—NMHis—ACHPA2f—Ile—AMP;

INOAc—His—ACHPA2f—Ile—AMP;

Ac—FTrp—Pro—Phe—NMHis—ACHPA2f—Ile—AMP;

Boc—Phe—His—ACHPA2f—MBA2S;

Boc—Phe—His—ACHPA2f—MBA3; and

Ac—NLAIS—His—ACHPA2f—Ile—AMP.

8. A compound of claim 2, selected from the group consisting of:

Boc—Phe—His—Sto$^{2f}$—Ile—AMP;

Boc—Phe—His—Sto$^{2f}$—Ile—AMP;

Boc—Phe—NMHis—ACOPA2f—Ile—AMP;

Boc—Pro—Phe—NMHis—ACOPA2f—Ile—AMP;

1NOAc—His—ACOPA2f—Ile—AMP;

Boc—Phe—His—ACOPA2f—MBA2S;

Ac—NLA1S—His—ACOPA2f—Ile—AMP; and

Boc—Phe—His—ACOPA2f—MBA3.

* * * * *

UNITED STATES PATENT OFFICE
CERTIFICATE OF CORRECTION

Patent No. 4,882,420           Dated   November 21, 1989

Inventor(s)   Suvit Thaisrivongs

It is certified that error appears in the above-identified patent and that said Letters Patent is hereby corrected as shown below:

Column 5, Line 40:
  "(o) -(CH$_{12}$)$_{0-4}$"

Column 28, line 54:

" -NHGC "

Signed and Sealed this

Third Day of March, 1992

Attest:

HARRY F. MANBECK, JR.

Attesting Officer     Commissioner of Patents and Trademarks